United States Patent [19]

Adrian et al.

[11] 4,241,226

[45] Dec. 23, 1980

[54] PREPARATION OF 2-NITRO-2-METHYL-1-PROPANOL

[75] Inventors: Guy Adrian, Lille; Marcel-Xavier Sion, Lewarde; Andre Benattar, Lille, all of France

[73] Assignee: Societe Chimique de la Grande Paroisse, Azote et Produits Chimiques, Paris, France

[21] Appl. No.: 12,440

[22] Filed: Feb. 15, 1979

[30] Foreign Application Priority Data

Feb. 15, 1978 [FR] France ............................. 78 04210

[51] Int. Cl.³ .......................................... C07C 79/18
[52] U.S. Cl. .................................................. 568/704
[58] Field of Search ........................................ 568/704

[56] References Cited

U.S. PATENT DOCUMENTS

| | | | |
|---|---|---|---|
| 2,132,330 | 10/1938 | Vanderbilt | 568/704 |
| 2,135,444 | 11/1938 | Vanderbilt | 568/704 |
| 2,139,120 | 12/1938 | Hass et al. | 568/704 |
| 3,534,112 | 10/1970 | Tindall | 568/704 |
| 3,560,575 | 2/1971 | Tindall | 568/704 |
| 3,564,062 | 2/1971 | Tindall | 568/704 |
| 3,651,144 | 3/1972 | Tindall | 568/704 |
| 3,655,781 | 4/1972 | Pringe | 568/704 |

FOREIGN PATENT DOCUMENTS

| | | | |
|---|---|---|---|
| 1046600 | 12/1958 | Fed. Rep. of Germany . | |
| 1590483 | 5/1970 | France . | |
| 942950 | 11/1963 | United Kingdom | 568/704 |
| 253038 | 2/1970 | U.S.S.R. | 568/704 |

OTHER PUBLICATIONS

Gorski et al. "Berichte" 67:996–1000 (1934).
Burmistrov et al., "C.A." 64:1523g (1966).
Vanderbilt et al., "I & E.C." vol. 32 (1940) p. 34.

*Primary Examiner*—Norman Morgenstern
*Attorney, Agent, or Firm*—Browdy and Neimark

[57] ABSTRACT

The known compound 2-nitro-2-methyl-1-propanol is prepared by formylation, in crystalline form of high purity and in high yields, by reacting 2-nitropropane and formaldehyde in a molar ratio between 0.9:1 and 1.1:1, in a concentrated medium and in the presence of 1 to 10 milli-equivalents of an inorganic basic catalyst per mole of 2-nitropropane, with agitation, at a temperature between 40° and 58° C.; the pH of the reaction medium being between 7 and 11.

4 Claims, No Drawings

PREPARATION OF 2-NITRO-2-METHYL-1-PROPANOL

FIELD OF INVENTION

This invention relates to the preparation of 2-nitro-2-methyl-1-propanol in crystalline form.

BACKGROUND

The standard preparation of 2-nitro-2-methyl-1-propanol by the action of formaldehyde on 2-nitropropane in a basic medium is known. The basic agent is used in molar proportions or preferably in catalytic amounts; and the bases used are generally alkali or alkaline-earth metal hydroxides, basic ion exchange resins or tertiary amines. The reaction is carried out in an aqueous or water-alcohol medium. After reaction and salification of the base, there follow the operations of concentration, selective extraction and crystallization in a suitable solvent. It is understood that these series of manipulations are long and tedious, further requiring recycling of the solvents used during condensation and crystallization, and resulting in an uneconomical process.

SUMMARY

An improved process has now been found that makes it possible to eliminate the concentration and selective extraction operations and consequently the recycling of the solvents, therefore mitigating the drawbacks of known processes. The new process isolates 2-nitro-2-methyl-1-propanol with a great purity directly from the neutralized reaction medium, and with yields that can be greater than 95%.

According to the invention 2-nitropropane and formaldehyde are contacted in a molar ratio between 0.9:1 and 1.1:1, in a concentrated medium and in the presence of 1 to 10 milliequivalents of an inorganic basic catalyst per mole of 2-nitropropane, with agitation for a period of 1 to 48 hours, at a temperature between 40° and 58° C., the pH of the reaction medium being between 7 and 11, and the 2-nitropropane and formaldehyde react under these conditions to directly produce the desired 2-nitro-2-methyl-1-propanol in crystalline form.

DETAILED DESCRIPTION OF EMBODIMENTS

The inorganic basic catalyst is advantageously selected from alkaline hydroxides such as potassium hydroxide or sodium hydroxide. It can be dissolved in water.

Keeping the pH of the reaction medium between 8 and 9 leads to very satisfactory results.

In general, the formaldehyde may be introduced mostly in the form of polyoxymethylene.

According to a particularly advantageous embodiment the reagents and catalyst are respectively put in reaction in the order 2-nitropropane, formaldehyde and basic catalyst and in the presence of an amount of water representing 1.5 to 10% by weight of the totality of the reaction mass. This slight amount of water can be introduced as aqueous formaldehyde solution.

After the reaction, the reaction mixture is then neutralized with acid at a temperature on the order of 55° C. The acid can be an inorganic or organic acid such as concentrated hydrochloric acid or stearic acid. Such neutralizing agent is added in an amount to lower the pH of the reaction mixture to between 4 and 5.

Crystallization of the 2-nitro-2-methyl propanol is progressive by cooling to ambient temperature or agitation with entraining, using a current of inert gas, of the water and volatile impurities of the raw reaction medium. A fine white powder is obtained with a purity above 95%, which can be directly shaped with a pellet machine or extruder.

The 2-nitro-2-methyl propanol has numerous applications particularly as an adhesion agent in making tires, a bactericide and a source of formaldehyde in a basic medium.

The examples given below illustrate the invention in a non-limiting way.

EXAMPLE 1

In an agitated flask that can be cooled by immersion in a bath of ice water, there are introduced 90.5 g of 2-nitropropane (1 mole) to which are added 8.7 g of an aqueous solution of 30% formol (0.08 moles), 1.2 g of sodium hydroxide in solution at 400 g/liter (0.008 moles) and gradually 29.8 g of polyoxymethylene (0.97 moles) so that the temperature is kept between 45° C. and 58° C. After 1 hour reaction at 50° C., neutralization with stearic acid at 55° C. is performed to pH=4.3 and the mixture is allowed to cool. The product is agitated under an air current so as to divide the clots of solid product that appear. After evaporation of the liquid phase, there are obtained 112.6 g (0.94 moles) of 2-nitro-2-methyl propanol as powder with a melting point of 88° C. The yield is 92% of a product whose microanalysis is correct, the purity being more than 95%.

EXAMPLE 2

As in example 1, there are introduced into a reactor 3572 g of 2-nitropropane (40 moles) to which are gradually and simultaneously added 87 g (0.8 mole) of 30% aqueous formol solution, 40 g (0.27 mole) of sodium hydroxide in solution at 400 g/liter and 1216 g of polyoxymethylene (40.5 moles). The reaction occurs slowly with the temperature of the medium between 44° and 55° C. for about 2 hours. Fifteen minutes after the end of the introduction of the polyoxymethylene, 70 g of stearic acid are introduced into the reaction medium which is then at 55° C. The rough weight of the resulting solution is then 4.8 kg.

The resultant hot solution of neutralized 2-nitro-2-methyl-1-propanol is then sent to the low point of a double-jacket inclined trough where two Archimedean screws with inserted blades turn in opposite directions. The movement of the screws tends to make the product rise toward the output at the high point of the trough; the double jacket of the trough is cooled with water to 15° C. At the top of the trough, closed by a cover, a flow of air or inert gas unsaturated with water circulates countercurrent to the product. The product, thus manipulated, cools, thickens, dries and crystallizes in a fine powder state. As a result, 4.35 kg of a product with a melting point of 88° C. are obtained. The yield is 91%. Microanalysis is correct and shows a purity of 95% after filtering.

Evacuation of the air blown over the trough is performed after dust removal and recovery of the 2-nitro-2-methyl-1-propanol entrained by techniques known in themselves. Yields greater than 95% are possible; the temperature of the cooling fluid of the double jacket, the rate of circulation of the product, the temperature and delivery of the drying gas circulating in the top determine the crystallization rate of the product.

EXAMPLE 3

There are put in reaction, in an agitated container cooled by a cold water bath, 136 g (1.5 moles) of 2-nitropropane to which are added 13 g of 30% aqueous formol solution (0.12 moles) and 1.5 g of sodium hydroxide at 400 g/liter (0.010 mole) and gradually 45 g of polyoxymethylene (1.42 moles). The product is allowed to cool and sent to the crystallization screw defined in example 2. There are obtained 163.2 g of a product with a melting point of 85° C., 92% yield of a product whose microanalysis is good.

EXAMPLE 4

Into the same container as used in example 3 are put into reaction 809 g (9.7 moles) of 2-nitropropane, 80 g of 30% aqueous formol solution (0.8 mole) and 15 g of sodium hydroxide solution at 400 g/liter in water; and there are then gradually added thereto 282.2 of polyoxymethylene (9.2 moles) during 1 hour. Neutralization is performed with concentrated HCl 15 minutes after the end of the introduction of the polyoxymethylene and the reaction mixture is allowed to cool to 45° C. before sending it to the endless screw defined in example 2. There are obtained 1109 g of a product with a melting point of 86° C. (96% yield) and whose microanalysis corresponds to 2-nitro-2-methyl-1-propanol.

It is to be understood that the invention is not limited to the embodiments disclosed which are illustratively offered and that modifications may be made without departing from the invention.

What is claimed is:

1. A process for the direct preparation of crystalline 2-nitro-2-methyl-1-propanol with a purity of at least 95%, by condensing 2-nitropropane with formaldehyde in a molar ratio of 0.9–1.1:1, consisting essentially of the steps of:
    adding less than half of the formaldehyde, in liquid form, to the 2-nitropropane and then adding 1 to 10 milliequivalents per mole of 2-nitropropane of an inorganic basic catalyst, water being present as the sole solvent in the amount of 1.5 to 10% of the totality of the reaction mass, after said additions;
    after said adding steps, progressively further adding with agitation the remainder of the formaldehyde in solid form of polyoxymethylene, maintaining the temperature between 40° and 58° C. and the pH between 7 and 11;
    neutralizing the formed reaction product at a temperature of about 55° C. with stearic acid up to a pH between 4 and 5; and
    cooling or agitating with entrainment, with a current of inert gas, of water and volatile impurities of the raw reaction medium.

2. Process of preparing 2-nitro-2-methyl-1-propanol according to claim 1 wherein the pH of the reaction medium is between 8 and 9.

3. Process of preparing 2-nitropropanol according to claim 1 or 2 wherein the basic catalyst is sodium hydroxide or potassium hydroxide.

4. Process of preparing 2-nitro-2-methyl-1-propanol according to claim 1 wherein the amount of water is introduced in the form of an aqueous formaldehyde solution.

* * * * *